(12) United States Patent
Senior

(10) Patent No.: US 6,194,189 B1
(45) Date of Patent: Feb. 27, 2001

(54) CATALYTICALLY-ACTIVE GELATINASE MUTANT

(75) Inventor: Robert M. Senior, St. Louis, MO (US)

(73) Assignee: Washington University, St. Louis, MO (US)

( * ) Notice: Subject to any disclaimer, the term of this patent is extended or adjusted under 35 U.S.C. 154(b) by 0 days.

(21) Appl. No.: 08/357,820

(22) Filed: Dec. 16, 1994

(51) Int. Cl.⁷ .............................. C12N 9/00; C12N 9/50; C07H 21/04
(52) U.S. Cl. .................... 435/219; 435/183; 536/23.2
(58) Field of Search ............... 435/219; 536/23.2

(56) References Cited

U.S. PATENT DOCUMENTS

| 4,992,537 | 2/1991 | Goldberg | 536/27 |
| 5,270,447 | * 12/1993 | Liotta et al. | 530/326 |

OTHER PUBLICATIONS

Senior et al., J. Biol. Chem. 266, 7870–75 (1991).
Murphy et al., Biochem. J. 277, 277–279 (1991).
Collier et al., J Biol. Chem. 267, 6776–6781 (1992).
Murphy et al., J. Biol. Chem. 269, 6632–6636 (1994).
Willenbrock et al., Biochemistry 32, 4330–37 (1993).
Wilhelm et al. J. Biol. Chem. 264, 17213–21 (1989).
Murphy et al., J. Biol. Chem. 267, 9612–9618 (1992).
O'Connell, J.P. et al. (1994) "Analysis of the role of the COOH–terminal domain in the activation, proteolytic activity, and tissue inhibitor of metalloproteinase interactions of gelatinase B" *J. Biol. Chem.* 269:14967–14973.*
Sequence comparison between SEQ ID No:1 and human metalloproteinase PUMP–1.*
Hirel, P.–H. et al. (1989) "Extent of N–terminal methionine excision from Escherichia coli proteins is governed by the side–chain length of the penultimate amino acid" Proc. Nat'l. Acad. Sci., USA 86:8247–8251, Nov. 1989.*
Thomas, J. et al. (1991) "Expression in Escherichia coli and characterization of the heat–stable inhibitor of the cAMP–dependent protein kinase" J. Biol. Chem. 266(17):10906–10911, Jun. 1991.*

* cited by examiner

*Primary Examiner*—Ponnathapua Achutamurthy
*Assistant Examiner*—Manjunath Rao
(74) *Attorney, Agent, or Firm*—Scott J. Meyer

(57) ABSTRACT

A truncated mutant of the 92 kDa gelatinase is disclosed which is catalytically active comparable to the full-length enzyme but, unlike the full-length enzyme, is essentially inactive against insoluble elastin. The truncated mutant preferably comprises residues 107–217 fused to residues 391–443 of the parent molecule. The truncated mutant is useful for treatment of disorders requiring the removal of excess connective tissue.

2 Claims, 2 Drawing Sheets

Figure 1:
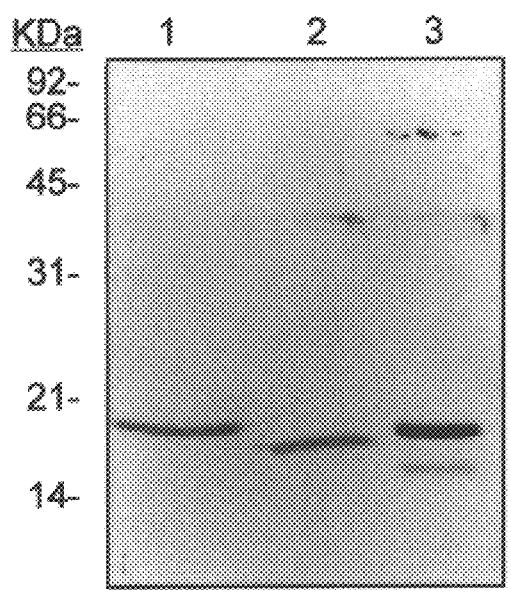

```
MAT CD   YSLFPNSPKWTSKVVTYRIVSYTRDLPHITVDRLVSKALNMWGKEIPLHFRKVVWGTADI
 92 CD   FQTFEGDLKWHHHNITYWIQNYSEDLPRAVIDDAFARAFALWSAVTPLIFTRVYSRDADI
 72 CD   YNFFPRKPKWDKNQITYRIHGYTPDLDPETVDDAFARAFQVWSDVTPLRFSRIHDGEADI

MAT CD   MIGFARGAHGDSYPFDGPGNTLAHAFAPGIGLGGDAHFDEDERWTDGSSLGINFLYAAIH
 92 CD   VIQFGVAEHGDGYPFDGKDGLLAHAFAPPGPGIQGDAHFDDDELWSLGKGVGYSLFVAAH
 72 CD   MINFGRWEHGDGYPFDGKDGLLAHAFAPGIGVGGDSHFDDDELWGFCPDQGYSLFVAAH

MAT CD   ELGHSLGMGHSSDPNAVMYPIYGNGDPQNFKLSQDDIKGIQKLYGKRSNSRKK
 92 CD   EFGHALGLDHSSVPEALMYPMYRF--TEGPPLHKDDVNGIRHLYG--------
 72 CD   EFGHAMGLEHSQDPGALMAPIYTY--TKNFRLSQDDIKGIQELYG----ASPDI
```

Fig. 2

CATALYTICALLY-ACTIVE GELATINASE MUTANT

"This invention was made in part with government support under grant number HL 47,328 awarded by the National Institutes of Health. The government has certain rights in the invention.

BACKGROUND OF THE INVENTION

The present invention relates to a truncated mutant of the 92 kDa gelatinase which is catalytically active comparable to the full protein but, unlike the full protein, is essentially inactive against insoluble elastin.

The truncated mutant of the invention is useful for treatment of disorders requiring the removal of excess connective tissue, e.g., keloids, post-operative fibrosis, intervertebral disc injections, hypertrophic scars, wound debridement, post-surgical adhesions and various fibrotic diseases (scleroderma, idiopathic pulmonary fibrosis) and the like treatments.

(Note: Literature references on the following background information, and on conventional test methods and laboratory procedures well known to the ordinary person skilled in the art, and other such state-of-the-art techniques as used herein are indicated in parentheses, and appended at the end of the specification.)

Elastin is an extracellular matrix protein composed of hydrophobic tropoelastin monomers that are highly crosslinked. Elastin provides resilience to elastic fibers. The hydrophobicity of tropoelastin monomers, as well as their extensive crosslinking, result in an insoluble elastic fiber which is highly resistant to proteolysis (1). In the normal physiologic state, elastin undergoes minimal turnover (2). However, pathologic situations exist including pulmonary emphysema (3) and abdominal aortic aneurysm (4) which are characterized by proteolytic destruction of elastic fibers.

The matrix metalloproteinases comprise a gene family of enzymes that collectively are capable of degrading all components of extracellular matrix in physiologic and pathologic states (5). These enzymes are organized into homologous domain structures, with some differences in number of domains. All members share a zymogen domain and a zinc-binding catalytic domain. As presently recognized, this family consists of fibroblast, neutrophil, and a breast carcinoma-derived (6) collagenase, a 92 kDa gelatinase (also called gelatinase B and MMP-9), a 72 kDa gelatinase (also called gelatinase A and MMP-2), three stromelysins, macrophage metalloelastase, matrilysin (also known as PUMP and MMP-7), and a recently described 66 kDa membrane-type metalloproteinase (7). Four members of this gene family have the capacity to degrade insoluble elastin. These are the 92 kDa gelatinase (8,9), the 72 kDa gelatinase (8,9), matrilysin (9), and macrophage metalloelastase The issue of substrate specificity has received considerable attention recently in matrix metalloproteinase biology. The structural determinants within these enzymes which confer the ability to degrade various substrates appear to be localized within discrete domains. For example, the ability of the collagenases to degrade triple-helical collagen requires the presence of the C-terminal hemopexin-like domain (12–14). In contrast, the stromelysins degrade a variety of substrates in a manner which is independent of the C-terminal hemopexin-like domain (13, 15–17). Unique to the 72 kDa and 92 kDa gelatinases is an additional domain composed of three fibronectin type II repeats inserted in tandem within the zinc-binding catalytic domain. This fibronectin-like domain is required for the gelatinases to bind efficiently to type I gelatin and type IV collagen (18–21). Matrilysin is the simplest member of this family of enzymes in that it contains only a zymogen domain and a catalytic zinc-binding domain.

A 92 kDa type IV collagenase (gelatinase) and the CDNA clone representing the full-length protein is disclosed in U.S. Pat. No. 4,992,537.

BRIEF DESCRIPTION OF THE INVENTION

In accordance with the present invention a truncated mutant of the 92 kDa gelatinase is provided which is catalytically active but essentially inactive against elastin. The truncated mutant preferably comprises residues 107–216 fused to residues 391–443 of the parent molecule.

This mutant representing the catalytic domain of the 92 kDa gelatinase has enzymatic activity against the conventional thiopeptolide substrate Ac-Pro-Leu-Gly-S-Leu-Leu-OEt comparable to the full-length 92 kDa gelatinase, and binds tissue inhibitor of metalloproteinases (TIMP) on an equimolar basis. It degrades gelatin but, surprisingly, it is inactive against insoluble elastin. The 92 kDa gelatinase, therefore, is unexpectedly unlike several other members of the matrix metalloproteinase family of enzymes such as matrilysin or macrophage metalloelastase in which the catalytic domains do account for elastolytic activity of these enzymes.

In accordance with a preferred embodiment of the invention, the catalytic zinc-binding domain of the 92 kDa gelatinase (92 CD) was expressed in E. coli. This gelatinase mutant was constructed such that it lacked the three fibronectin type II repeats contained within the catalytic domain of the native form of the enzyme. These internal fibronectin repeats were deleted by conventional polymerase chain reaction (PCR) procedures and the 92 CD was subcloned into a suitable expression vector for expression in E. coli. The resulting fragment coded for a protein lacking residues 217–390 of the parent molecule which encompass the three fibronectin-like repeats. A stop codon was placed after residue 443 to eliminate the collagen type V and hemopexin-like domains. The truncated mutant contained an additional Met-Gly dipeptide at the N-terminus in order to start translation at this point within the cDNA.

The protein sequence of the 92 CD, using the three-letter abbreviations of the constituent amino acid residues, is as follows:

```
Phe Gln Thr Phe Glu Gly Asp Leu Lys Trp His His His Asn Ile  [SEQ ID NO:1]
              5                   10                  15

Thr Tyr Trp Ile Gln Asn Tyr Ser Glu Asp Leu Pro Arg Ala Val
              20                  25                  30

Ile Asp Asp Ala Phe Ala Arg Ala Phe Ala Leu Trp Ser Ala Val
              35                  40                  45
```

-continued

```
Thr Pro Leu Thr Phe Thr Arg Val Tyr Ser Arg Asp Ala Asp Ile
            50              55              60

Val Ile Gln Phe Gly Val Ala Glu His Gly Asp Gly Tyr Pro Phe
            65              70              75

Asp Gly Lys Asp Gly Leu Leu Ala His Ala Phe Pro Pro Gly Pro
            80              85              90

Gly Ile Gln Gly Asp Ala His Phe Asp Asp Glu Leu Trp Ser
            95              100             105

Leu Gly Lys Gly Val Gly Tyr Ser Leu Phe Leu Val Ala Ala His
            110             115             120

Glu Phe Gly His Ala Leu Gly Leu Asp His Ser Ser Val Pro Glu
            125             130             135

Ala Leu Met Tyr Pro Met Tyr Arg Phe Thr Glu Gly Pro Pro Leu
            140             145             150

His Lys Asp Asp Val Asn Gly Ile Arg His Leu Tyr Gly
            155             160
```

It is known that interstitial collagenases and stromelysins have virtually no elastolytic activity, whereas matrilysin, macrophage metalloelastase, and the 92 kDa and 72 kDa gelatinases are elastolytic (8–11). Thus, the property of degrading insoluble elastin is restricted to select members of the matrix metallo-proteinase family. However, the overall homology among the elastolytic metalloproteinases does not distinguish them from the non-elastolytic members of the family. In fact, the elastolytic matrix metalloproteinases are as similar to fibroblast collagenase, a non-elastolytic enzyme, as they are to each other.

In view of the above, regions of these enzymes, including the 92 kDa gelatinase, which may be involved in elastin binding and degradation, are not obvious by comparison to one another or to non-elastolytic matrix metalloproteinases. The finding herein that the 92 CD is essentially inactive against insoluble elastin is an unexpected and advantageous property. This permits effective activity for the excess connective tissue conditions mentioned hereinabove because in such circumstances excessive elastin accumulation is not a particular feature. Because matrilysin and macrophage metalloelastase are functional elastases consisting only of the typical catalytic zinc-binding domain in their activated forms, it was expected that the catalytic domain of the 92 kDa gelatinase likewise would be functional against elastin.

The 92 CD truncated mutant has the additional advantages in that it can be produced readily in large quantities in bacteria (e.g., E. coli) and is easily purified. Moreover, unlike the full-length enzyme, it does not require activation in order to be enzymatically active.

DETAILED DESCRIPTION OF THE INVENTION

While the specification concludes with claims particularly pointing out and distinctly claiming the subject matter regarded as forming the present invention, it is believed that the invention will be better understood from the following detailed description of preferred embodiments of the invention taken in conjunction with the appended drawings in which:

FIG. 1 shows the SDS-PAGE of the matrilysin CD, 92 CD, and 72 CD expressed in E.coli. The catalytic domains of matrilysin, the 92 kDa gelatinase, and the 72 kDa gelatinase were expressed in E.coli and purified as described below in the "Materials and Methods". The predicted molecular masses are 19,297, 18,428, and 19,154 daltons for the matrilysin CD (lane 1), 92 CD (lane 2), and 72 CD (lane 3), respectively. The minor band in lane 3 represents autoprocessing of the 72 CD.

FIG. 2 shows the alignment of the peptide sequences of the catalytic domains of matrilysin, the 72 kDa gelatinase, and the 92 kDa gelatinase. The peptide sequences of the matrilysin, 72 kDa gelatinase, and 92 kDa gelatinase catalytic domains were aligned using the GENEWORKS program (Intelligenetics). Residues of identity amongst the three enzymes are boxed. Gaps are indicated by dashes. The Met-Gly dipeptide (matrilysin CD and 92 CD) and the met-ala-ser tripeptide (72 CD) that were introduced to initiate translation of the catalytic domains are not shown. The fibronectin-like type II repeats located within the 92 CD and 72 CD have been deleted.

Figure 3:
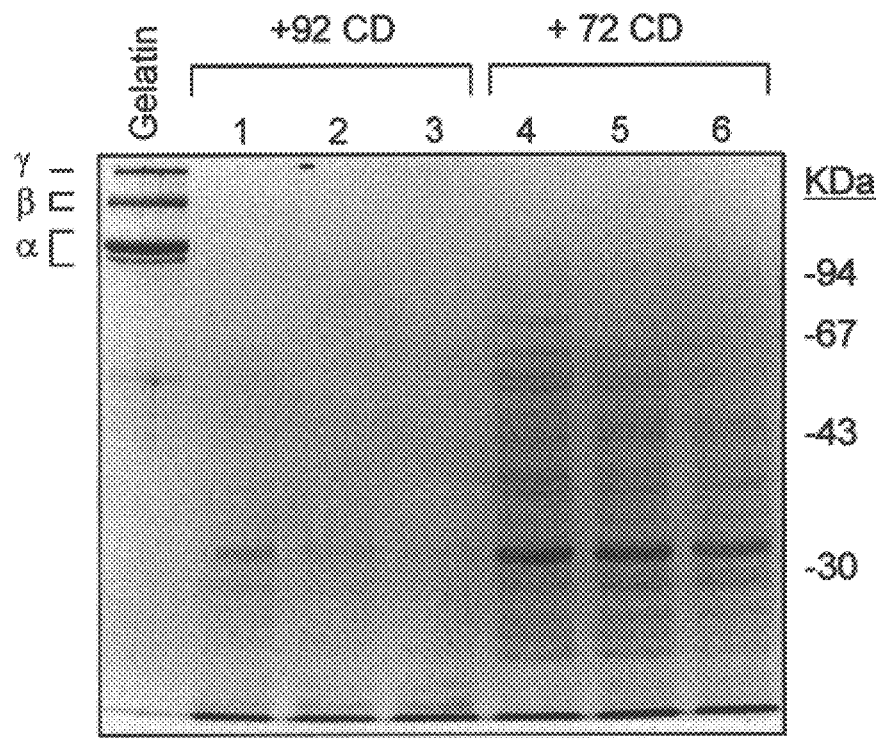

FIG. 3 shows the digestion of type I gelatin by the 92 CD and 72 CD. The 92 CD and 72 CD (1.3 $\mu$g/ml) were incubated with 10 $\mu$g of gelatin for 20 min (lanes 1 and 4), 40 min (lanes 2 and 5), and 60 min (lanes 3 and 6) as described below under "Materials and Methods". Reaction aliquots were boiled in sample buffer and subject to SDS-PAGE.

In order to illustrate the invention in further detail, the following specific laboratory examples were carried out with the results as indicated. Although specific examples are thus illustrated, it will be understood that the invention is not limited to these specific examples or the details therein.

EXAMPLES

Materials and Methods

Reagents:

Bovine ligament elastin and human leukocyte elastase (HLE) were obtained from Elastin Products, Owensville, Mo. The ligament elastin was radiolabeled with [$^3$H] sodium borohydride (DuPont-New England Nuclear) to a specific activity of~1000 cpm/$\mu$g (22).

Isopropylthio-$\beta$-D-galactopyranoside (IPTG), heparin agarose, aminophenylmercuric acetate (APMA), 5,5'-dithio-bis-(2-nitrobenzoic acid) (DTNB), trypsin, and soybean trypsin inhibitor (SBTI) were from Sigma Chemical, St. Louis, Mo.

Ac-Pro-Leu-Gly-S-Leu-Leu-Gly-OEt (thiopeptolide) was obtained from Bachem Bioscience, King of Prussia, Pa.

72 kDa gelatinase, recombinantly expressed in vaccinia virus and free of TIMP-2 (23), was kindly provided by W. Stetler-Stevenson, National Cancer Institute, Bethesda, Md.

Recombinant TIMP-1 was purified from the conditioned medium of human skin fibroblast monolayer cell cultures reported previously (24).

Bovine dermal type I collagen (Vitrogen 100) was from CELLTRIX, Palo Alto, Calif.

Expression and purification of full-length 92 kDa gelatinase and matrilysin. 92 kDa gelatinase was expressed in E1A- and 92 kDa gelatinase-transfected fibroblasts and purified to homogeneity as previously described (25). In this system, the 92 kDa enzyme is obtained free of TIMP. The 92 kDa progelatinase was activated with stromelysin-1 as previously reported (26), or with 1 mM APHA. Prostromelysin was purified from cultures of IL-1-stimulated fibroblasts and was activated by sequential exposure to trypsin and SBT1 as previously described (27).

Matrilysin was expressed and purified using a baculovirus expression system (28). A 1.1 kb Eco RI fragment encoding the human matrilysin cDNA (kindly provided by L. Matrisian, Vanderbilt) was subcloned in the baculovirus expression vector pVL1393 (Pharmingen) and expressed in Sf9 insect cells (ATCC CRL 1711) according to the manufacturer's instructions.

The viral titer of the transfection supernatant was amplified by two additional rounds of infection to obtain a titer of $4 \times 10^8$ pfu/ml. For large scale production of matrilysin, Sf9 cells were seeded in spinner culture at $2 \times 10^6$ cells/ml in Sf-900 II serum-free media (Gibco BRL) at a multiplicity of infection of 2 virus particles/cell.

Media containing~5 µg/ml matrilysin in the zymogen form was collected at four days post-infection for purification of the secreted enzyme. Serum-free collections of media were bound to SP-Sepharose in 25 mM Tris, pH 7.5, 5 mM $CaCl_2$, 30 mM NaCl and washed in the same buffer. The sample was eluted in this buffer containing 300 mM NaCl in a volume of 50 ml and concentrated to 3 ml with a Filtron concentrator (Filtron Corporation) prior to gel filtration.

100 µl aliquots were loaded on a Superdex-75 HR 10/30 gel filtration column (Waters 650E Advanced Protein Purification System) previously equilibrated in 50 mM Tris, pH 7.5,5 mM $CaCl_2$, 200 mM NaCl, 0.02% $NaN_3$. The peak corresponding to the purified enzyme, eluting at 26 minutes, was collected.

Expression of the matrilysin CD and the 92 kDa and 72 kDa gelatinase CDs lacking the internal fibronectin type II repeats. Matrilysin and 92 kDa gelatinase catalytic domain constructs were generated by PCR and subcloned into the pET-14b expression vector (Novagen, Madison, Wis.) for expression in E.coli.

The forward matrilysin primer (5'GGATATCCATGGGTT ACTCACTATTTCCAAATAG3'[SEQ. ID NO: 2] contained an Nco I site, while the reverse primer (5'GCCGAGATCTTGATCAA TTCTGATTGTGCAA3') [SEQ. ID NO: 3] contained a Bgl II site to facilitate subcloning into the expression vector.

For construction of the 92 CD without the fibronectin repeats, the internal fibronectin type II repeats were deleted by recombinant PCR (29).

The region of the catalytic domain 5' to the fibronectin repeats was amplified with the primers (5' CTGTGCCATGGGATTCCAAACCTTTGAG3') [SEQ. ID NO:4] and (5'CGAGGAACAAACTGTATCCGACGCCCTTGCC CAGGG3') [SEQ. ID NO:5] while the region 3' to the fibronectin repeats was amplified with the primers (5'CCCTGGGCAAGGGCGTCGGA TACAGTTTGTTCCTCG3') [SEQ. ID NO:6] and (5'CAACTCTCGAGTCAACCATAGAGGTGCCG3') [SEQ. ID NO:7].

After gel purification of both PCR products, the products were annealed to each other by virtue of the complimentary design of the internal PCR primers, and amplified using the outside primers. The resulting fragment coded for a protein lacking residues 217–390 of the parent molecule which encompass the three fibronectin-like repeats.

A stop codon was placed after residue 443 in this construct as well, thereby eliminating the collagen type V and hemopexin-like domains. Thus, the matrilysin CD contained residues 95–267 of the parent molecule, and the 92 CD contained residues 107–216 fused to residues 391–443. Both the matrilysin and 92 kDa gelatinase constructs contained an additional Met-Gly dipeptide at the N-terminus in order to start translation at this point within the cDNA.

The resulting matrilysin CD and 92 CD constructs in pET-14*b* were transformed into the E.coli BL21(DE3) strain (Novagen) for expression. Colonies were grown in 10 ml LB media containing 50 µg/ml ampicillin to log phase and induced with 0.4 mM IPTG for four hours. After centrifugation, the pellets were re-suspended in 2.5 ml of 50 mM Tris, pH 7.5, 10 mM $CaCl_2$, 30 mM NaCl and sonicated 5×15 seconds on ice. 8 M deionized urea was added to a final concentration of 6 M and the extract was rocked gently at 4° C. overnight, prior to centrifugation at 10,000 rpm for 10 minutes in a Sorvall SS34 rotor.

The samples were dialyzed successively against 4 M, 2 M, and 1 M urea in the same buffer containing 20 µM $ZnCl_2$ and 0.05% Brij and finally against urea-free buffer. The matrilysin CD was purified over a 1 ml heparin-agarose column and eluted in the same buffer containing 1 M NaCl. The sample was redialyzed against the equilibration buffer containing 30 mM NaCl. The 92 CD was dialyzed stepwise as described above except that zinc was removed in the final dialysis step containing no urea.

This product was purified over a 1 ml Zn chelate chromatography column, and bound material was eluted in equilibration buffer containing 0.1M imidazole. Imidazole was removed by further dialysis against equilibration buffer. The 72 CD was expressed in E. coli, as recently described (20). Briefly, a synthetic gene coding for the 72 CD (lacking the fibronectin repeats) was generated by PCR, inserted into the vector pGEMEX-1, and used to transform the E. coli strain BL21(DE3)pLysS (Novagen, Madison, Wis.). The synthetic gene included restriction sites for Nhe I at the 5' end and Hind III at the 3' end of the gene. This construct contained an additional Met-Ala-Ser tripeptide at the amino-terminus to initiate translation of the synthetic gene, and the methionine was removed during E. coli expression. The resulting protein contained residues 110–213 of the parent molecule fused to residues 387–444. The authenticity of the expressed 72 CD was confirmed by N-terminal amino acid sequencing.

Assays:

Elastase activity: Elastase activity was determined by quantifying the solubilization of insoluble $^3$H-labeled elastin (22). Reactions were carried out at 37° C. in 50 mM Tris HCl(pH 7.5), 10 mM $CaCl_2$, 150 mM NaCl, 0.02% Brij, in a final volume of 100 µl with an excess of elastin (~70 µg). Following centrifugation, radioactivity released into the supernatant was collected and counted. Buffer blanks were subtracted to determine net values. Initial velocities were calculated in ranges which were linear over time and enzyme concentration. When assaying 92 kDa gelatinase, blanks also contained stromelysin-1 which was used to activate the gelatinase. The activity of the stromelysin was negligible in these assays. For assays of 72 CD, the buffer included 1 µM $ZnCl_2$ (20).

Hydrolysis of Ac-Pro-Leu-Gly-S-Leu-Leu-Gly-OEt (thiopeptolide): Hydrolysis of the thiopeptolide substrate was determined as previously described (30). Accordingly, 7 mg of the thiopeptolide substrate was dissolved in 50 µl methanol and brought to 1 ml by the addition of 950 µl of assay buffer (0.05 M HEPES, pH 7.0, 0.01 M $CaCl_2$). DTNB, 40 mg, was dissolved in 2 ml ethanol and brought up to 10 ml with assay buffer. Reaction mixtures contained 100 µl each of enzyme solution and DTNB and 10 µl of the thiopetiolide substrate in a total volume of 1 ml. Reactions were run at room temperature and monitored at 410 nanometers (A410) (Gilford RESPONSE) for the first five minutes after the addition of enzyme. $ZnCl_2$ was added to a final concentration of 1 µM to ensure activity when assaying the 72 CD.

Hydrolysis of gelatin: Type I collagen was dialyzed against 400 mM NaCl and then denatured by heating at 60° C. for 15 min. To determine the gelatinolytic activity of the full-length 92 kDa and 72 kDa gelatinases and their catalytic domains, enzymes were incubated at 37° C. for periods up to 60 minutes with 10 µg of gelatin in a final volume of 60 µl containing 50 mM Tris HCl (pH 7.5), 10 mM $CaCl_2$, 400 mM NaCl, 0.001 mM $ZnCl_2$. Aliquots of the reaction mixtures were mixed with sample buffer and dithiothreitol and subjected to SDS-PAGE, after which gels were stained with Coomassie Blue.

Binding of full-length 92 kDa and 72 kDa gelatinases, the 92 CD. and the 72 CD to insoluble elastin: To determine binding to elastin, full-length enzymes or catalytic domain mutants were mixed with 63 µg of insoluble elastin for 10 min at room temperature, after which the mixture was centrifuged for 30 sec and the supernatant removed and analyzed for activity against the thiopeptolide substrate as described above. The thiopeptolide activity was compared to control reaction mixtures in which the full-length gelatinase or CD was not exposed to insoluble elastin. Binding to elastin was expressed as the percent reduction in thiopeptolide activity produced by incubation with elastin.

RESULTS:

Expression and purification of the matrilysin CD, 92 CD, and 72 CD: The expressed matrilysin CD, 92 CD, and 72 CD are shown in FIG. 1. Purification as described under Materials and Methods yielded a single electrophoretic band for each species of $M_r$—20,000. The amino acid sequences of the matrilysin CD and the gelatinase CDs (with the fibronectin repeats deleted) are shown in FIG. 2. While all three parent molecules are elastolytic, the catalytic domains of each share no more homology with each other (43–60%) than they do to fibroblast collagenase, a nonelastolytic matrix metallo-proteinase. Consequently, regions which might be involved in elastin-degrading functions are not obvious by inspection of these sequences.

Catalytic activities of full-length matrilysin, 92 kDa and 72 kDa gelatinases versus their respective catalytic domains: TABLE 1 below presents the activities of full-length matrilysin, the 92 kDa and 72 kDa gelatinases and the respective catalytic domains of these molecules against both insoluble elastin and a synthetic thiopeptolide substrate. Activity against the thiopeptolide substrate was used to assess the general catalytic competence of native and mutant enzymes.

As seen in the Table, each catalytic domain possessed comparable specific activity to its respective full-length parent against this thiopeptolide substrate. However, this was clearly not the case when capacity to cleave insoluble elastin was measured. As would be expected, the matrilysin CD exhibited identical elastolytic activity to its APMA-activated parent, since they are indeed the same. In contrast, whereas the full-length 92 kDa and 72 kDa gelatinases exhibited substantial ability to cleave insoluble elastin, the 92 CD and 72 CD unexpectedly had little to no elastolytic activity. Even very high molar concentrations of the 92 CD and 72 CDs (in excess of 500 µg/ml) produced only barely detectable activity against elastin. However, inability of the 92 CD and 72 CD to degrade elastin did not extend to other proteins, as both domains digested gelatin (FIG. 3).

Binding of the 92 CD and 72 CD to elastin: To determine whether the relative inabilities of the 92 CD and 72 CD to degrade elastin related to their capacity to bind to this substrate, elastin binding was assayed, again in comparison to the full-length parent molecules. As shown in TABLE II below, the full-length 92 kDa and 72 kDa gelatinases demonstrated substantial binding to insoluble elastin. In sharp contrast, the 92 CD and 72 CD showed virtually no binding to elastin. It is concluded that the failure of the 92 and 72 CDs to degrade elastin is most likely a result of their failure to bind effectively to this substrate.

TABLE I

Comparison of Activities of Full Length Metalloproteinases to their Catalytic Domain Constructs Against Insoluble Elastin and Thiopeptolide

|  | $^3$H-Elastin (cpm released/hr) | Thiopeptolide ($\Delta OD_{410}$/min) |
| --- | --- | --- |
| 92 kDa gelatinase | 1173 | 0.0390 |
| 92 CD | 26 | 0.0836 |
| 72 kDa gelatinase | 1272 | 0.0416 |
| 72 CD | 0 | 0.0415 |
| Matrilysin | 619 | 0.0337 |
| MAT CD | 531 | 0.0458 |

Results represent the mean of three or more separate assays. For assays with elastin, enzyme concentrations were 1 µg/ml (1–5×10$^{-8}$ M). The minimal to absent levels of elastolytic activity of the 92 CD and 72 CD at 10$^{-8}$ M were confirmed at domain concentrations of 10$^{-6}$ M and 10$^{-7}$ M. For thiopeptolide assays, enzymes and domains were used at 5×10$^{-8}$ M. Elastin assays were for one hour and thiopeptolide assays for five minutes.

TABLE II

Binding of the 92 kDa and 72 kDa Gelatinases and Their Catalytic Domains to Insoluble Elastin

| Enzyme | Thiopeptolide activity* | Thiopeptolide activity* after elastin exposure | % Bound |
| --- | --- | --- | --- |
| 92 kDa gelatinase | 0.0390 | 0.0203 | 48% |
| 92 kDa CD | 0.0836 | 0.0843 | 0% |
| 72 kDa gelatinase | 0.0416 | 0.0210 | 50% |
| 72 kDa CD | 0.0415 | 0.0377 | 9% |

*$\Delta OD_{410}$/ min

Enzymes (10$^{-8}$ M) were incubated for 10 minutes at room temperature in the presence or absence of 63 µg of insoluble elastin. After centrifugation, the supernatants were assayed for activity against the thiopeptolide substrate. The percent of enzyme bound to elastin was determined using the formula % bound =[1−(supernatant+elastin−supernatant−elastin)] ×100.

REFERENCES

1) Mecham, R. P. & Heuser, J. E. (1991). The elastic fiber. In E. D. Hay (Ed.), *Cell Biology of Extracellular Matrix* (pp. 79–109). New York: Plenum.

2) Shapiro, S. D., Endicott, S. K.. Province, M. A., Pierce, J. A., and Campbell. E. J. (1991). *J. Clin. Invest.*, 87: 1828–1834.

3) Janoff, A. (1985). *Am. Rev. Respir. Dis.*, 132: 417–433.

4) Brophy, C. M., Reilly. J. M., Smith. G. J. W., & Tilson, M. D. (1991). *Ann. Vasc. Surg.*, 5:229–233.

5) Murphy, G.. & Docherty, A. J. P. ( 1992). *Am. J. Respir. Cell Mol. Biol.*, 7: 120–125.

6) Freije, J. M. P., Diez-Itza, I., Balbin. M., Sanchez, L. M., Blasco, R., Tolivia, J., & Lopez-Otin, C. (1994). *J. Biol. Chem.*, 269: 16766–16773.

7) Sato, H., Takino, T., Okada. Y., Cao, J., Shinagawa, A., Yamamoto, E., & Seiki, M. (1994). *Nature*, 370: 61–65.

8) Senior, R. M., Griffin. G. L., Fliszar, C. J., Shapiro, S. D., Goldberg, G. I., & Welgus, H. G. (1991). *J. Biol. Chem.*, 266: 7870–7875.

9) Murphy, G., Cockett, M. I., Ward, R. V., & Docherty, A. J. P. (1991). *Biochem. J.*, 277: 277–279.

10) Shapiro, S. D., Griffin, G. L., Gilbert, D. J., Jenkins, N. A., Copeland, N. G., Welgus, H. G., Senior, R. M., & Ley. T. J. (1992). *J. Biol. Chem.*, 267: 4664–4671.

11) Shapiro, S. D., D. K. Kobayashi, and T. J. Ley (1993). *J. Biol. Chem.*, 268: 23824–23829.

12) Schnierer. S., Kleine, T., Gote, T., Hillemann, A., Knauper, V., & Tschesche, H. (1993). *Biochem. Biophys. Res. Commun.*, 191: 319–326.

13) Sanchez-Lopez. R., Alexander, C. M., Behrendtsen, O., Breathnach, R., & Werb, Z. (1993). *J. Biol. Chem.*, 268: 7238–7247.

14) Hirose, T., Patterson, C., Pourmotabbed, T., Mainardi, C. L., & Hasty. K. A. (1993). *Proc. Natl. Acad. Sci. USA*. 90: 2569–2573.

15) Sanchez-Lopez R., Nicholson, R., Gesnel, M.-C., Matrisian, L. M., & Breathnach, R. (1988). *J. Biol. Chem.*, 263: 11892–11899.

16) Marcy, A. I., Eiberger, L. L., Harrison, R., Chan, H. K., Hutchinson, N. I., Hagmann, W. K., Cameron, P. M., Boulton, D. A., & Hermes, J. D. (1991). *Biochemistry*, 30: 6476–6483.

17) Ye, Q.-Z., Johnson. L. L., Hupe. D. J., & Baragi, V. (1992). *Biochemistry*, 31: 11231–11235.

18) Collier, I. E., Krasnov. P. A., Strongin, A. Y., Birkedal-Hansen, H., & Goldberg, G. I. (1992). *J. Biol. Chem.*, 267: 6776–6781.

19) Murphy, G., Nguyen, Q., Cockett, M. I., Atkinson, S. J., Allan, J. A., Knight, C. G., Willenbrock, F., & Docherty, A. J. P. (1994). *J. Biol. Chem.*, 269: 6632–6636.

20) Ye, Q.-Z., Johnson. L. L., Yu, A. E., & Hupe, D. (1994). submitted.

21) Banyai, L., Tordai. H., & Patthy. L. (1994). *Biochem. J.*, 298:403–407.

22) Banda, M. J., Dovey, H. F., & Werb, Z. (1981). Elastinolytic enzymes. In D. O. Adams, P. J. Edelson, & H. Koren (Eds.), *Methods for studying mononuclear phagocytes* (pp. 603–618). New York: Academic Press.

23) Fridman, R., Fuerst. T. R., Bird, R. E., Hoyhtya, M., Oelkuct, M., Kraus, S., Komarek, D., Liotta. L. A., Berman. M. L., & Stetler-Stevenson, W. G. (1992) *J. Biol. Chem.* 267: 15398–15405.

24) Stricklin, G. P., & Welgus, H. G. (1983). *J. Biol. Chem.*, 258: 12252–12258.

25) Frisch, S. M., Reich, R., Collier. I. E., Genrich. L. T., Martin, G., & Goldberg, G. I., (1990). *Oncogene*, 5: 75–83.

26) Ogata, Y., Enghild, J. J., & Nagase, H. (1992). *J. Biol. Chem.*, 267: 3581–3584.

27) Wilhelm, S. M., Collier. I. E., Kroneberger, A., Eisen, A. Z., Marmer, B. L., Grant, G. A., Bauer, E. A., & Goldberig, G. I. (1987). *Proc. Natl. Acad. Sci. U.S.A.*, 84: 6725–6729.

28) Baragi, V. M., Fliszar, C. J., Conoy, M. C., Ye, Q.-Z, Shipley, J. M., & Welgus, H. G. (1994). *J. Biol. Chem.*, 269: 12692–12697.

29) Higuchi, R., Krummel, B., & Saiki, R. K. (1988). *Nucleic Acids Res.*, 16: 7351–7367.

30) Weingarten, H., & Feder, J. (1985). *Anal. Biochem.*, 147: 437–440.

31) Welgus, H. G., Jeffrey, J. J., & Eisen, A. Z. (1981). *J. Biol. Chem.*, 256: 9516–9521.

32) Sires, U. I., Griffin, G. L., Broekelmann, T. J., Mecham, R. P., Murphy, G., Chung, A. E., Welgus, H. G., & Senior, R. M. (1993). *J. Biol. Chem.*, 268: 2069–2074.

33) Welgus, H. G., Burgeson, R. E., Wooton, J. A. M., Minor, R. R., Fliszar, C., and Jeffrey. J. J. (1985) J. Biol. Chem. 260: 1052–1059.

SEQUENCE LISTING (1) GENERAL INFORMATION:

(iii) NUMBER OF SEQUENCES: 9

(2) INFORMATION FOR SEQ ID NO:1:

(i) SEQUENCE CHARACTERISTICS:
      (A) LENGTH: 163 amino acids
      (B) TYPE: amino acid
      (C) STRANDEDNESS:
      (D) TOPOLOGY: linear (ii) MOLECULE TYPE: peptide (xi) SEQUENCE DESCRIPTION: SEQ ID NO:1:

Phe Gln Thr Phe Glu Gly Asp Leu Lys Trp His His His Asn Ile Thr
1               5                   10                  15

Tyr Trp Ile Gln Asn Tyr Ser Glu Asp Leu Pro Arg Ala Val Ile Asp
                20                  25                  30

Asp Ala Phe Ala Arg Ala Phe Ala Leu Trp Ser Ala Val Thr Pro Leu
            35                  40                  45

Thr Phe Thr Arg Val Tyr Ser Arg Asp Ala Asp Ile Val Ile Gln Phe
    50                  55                  60

Gly Val Ala Glu His Gly Asp Gly Tyr Pro Phe Asp Gly Lys Asp Gly
65                  70                  75                  80

Leu Leu Ala His Ala Phe Pro Pro Gly Pro Gly Ile Gln Gly Asp Ala
                85                  90                  95

His Phe Asp Asp Asp Glu Leu Trp Ser Leu Gly Lys Gly Val Gly Tyr
                100                 105                 110

Ser Leu Phe Leu Val Ala Ala His Glu Phe Gly His Ala Leu Gly Leu
            115                 120                 125

Asp His Ser Ser Val Pro Glu Ala Leu Met Tyr Pro Met Tyr Arg Phe
130                 135                 140

Thr Glu Gly Pro Pro Leu His Lys Asp Asp Val Asn Gly Ile Arg His
145                 150                 155                 160

Leu Tyr Gly (2) INFORMATION FOR SEQ ID NO:2:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic DNA"

(xi) SEQUENCE DESCRIPTION: SEQ ID NO:2:

GGATATCCAT GGGTTACTCA CTATTTCCAA ATAG                        34

(2) INFORMATION FOR SEQ ID NO:3:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic DNA"

(xi) SEQUENCE DESCRIPTION: SEQ ID NO:3:

GCCGAGATCT TGATCAATTC TGATTGTGCA A                           31

(2) INFORMATION FOR SEQ ID NO:4:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: other nucleic acid (A) DESCRIPTION: /desc = "Synthetic DNA"

(xi) SEQUENCE DESCRIPTION: SEQ ID NO:4:

CTGTGCCATG GGATTCCAAA CCTTTGAG                                28

(2) INFORMATION FOR SEQ ID NO:5:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic DNA"

(xi) SEQUENCE DESCRIPTION: SEQ ID NO:5:

CGAGGAACAA ACTGTATCCG ACGCCCTTGC CCAGGG                        36

(2) INFORMATION FOR SEQ ID NO:6:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic DNA"

(xi) SEQUENCE DESCRIPTION: SEQ ID NO:6:

CCCTGGGCAA GGGCGTCGGA TACAGTTTGT TCCTCG                        36

(2) INFORMATION FOR SEQ ID NO:7:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic DNA"

(xi) SEQUENCE DESCRIPTION: SEQ ID NO:7:

CAACTCTCGA GTCAACCATA GAGGTGCCG                               29

(2) INFORMATION FOR SEQ ID NO:8:

(i) SEQUENCE CHARACTERISTICS:
        (A) LENGTH: 173 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:8:

Tyr Ser Leu Phe Pro Asn Ser Pro Lys Trp Thr Ser Lys Val Val Thr
1               5                   10                  15

Tyr Arg Ile Val Ser Tyr Thr Arg Asp Leu Pro His Ile Thr Val Asp
            20                  25                  30

Arg Leu Val Ser Lys Ala Leu Asn Met Tyr Gly Lys Glu Ile Pro Leu
        35                  40                  45

His Phe Arg Lys Val Val Trp Gly Thr Ala Asp Ile Met Ile Gly Phe
    50                  55                  60

```
Ala Arg Gly Ala His Gly Asp Ser Tyr Pro Phe Asp Gly Pro Gly Asn
 65                  70                  75                  80

Thr Leu Ala His Ala Phe Ala Pro Gly Thr Gly Leu Gly Gly Asp Ala
                 85                  90                  95

His Phe Asp Glu Asp Glu Arg Trp Thr Asp Gly Ser Ser Leu Gly Ile
            100                 105                 110

Asn Phe Leu Tyr Ala Ala Thr His Glu Leu Gly His Ser Leu Gly Met
            115                 120                 125

Gly His Ser Ser Asp Pro Asn Ala Val Met Tyr Pro Thr Tyr Gly Asn
            130                 135                 140

Gly Asp Pro Gln Asn Phe Lys Leu Ser Gln Asp Asp Ile Lys Gly Ile
145                 150                 155                 160

Gln Lys Leu Tyr Gly Lys Arg Ser Asn Ser Arg Lys Lys
                165                 170
```

(2) INFORMATION FOR SEQ ID NO:9:

(i) SEQUENCE CHARACTERISTICS:
        (A) LENGTH: 168 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:9:

```
Tyr Asn Phe Phe Pro Arg Lys Pro Lys Trp Asp Lys Asn Gln Ile Thr
 1               5                  10                  15

Tyr Arg Ile Ile Gly Tyr Thr Pro Asp Leu Asp Pro Glu Thr Val Asp
                 20                  25                  30

Asp Ala Phe Ala Arg Ala Phe Gln Val Trp Ser Asp Val Thr Pro Leu
            35                  40                  45

Arg Phe Ser Arg Ile His Asp Gly Glu Ala Asp Ile Met Ile Asn Phe
            50                  55                  60

Gly Arg Trp Glu His Gly Asp Gly Tyr Pro Phe Asp Gly Lys Asp Gly
 65                  70                  75                  80

Leu Leu Ala His Ala Phe Ala Pro Gly Thr Gly Val Gly Gly Asp Ser
                 85                  90                  95

His Phe Asp Asp Asp Glu Leu Trp Gly Phe Cys Pro Asp Gln Gly Tyr
            100                 105                 110

Ser Leu Phe Leu Val Ala Ala His Glu Phe Gly His Ala Met Gly Leu
            115                 120                 125

Glu His Ser Gln Asp Pro Gly Ala Leu Met Ala Pro Ile Tyr Thr Tyr
            130                 135                 140

Thr Lys Asn Phe Arg Leu Ser Gln Asp Asp Ile Lys Gly Ile Gln Glu
145                 150                 155                 160

Leu Tyr Gly Ala Ser Pro Asp Ile
                165
```

Various other examples will be apparent to the person skilled in the art after reading the present disclosure without departing from the spirit and scope of the invention. It is intended that all such other examples be included within the claims appended hereto.

What is claimed:

1. The cDNA sequence which encodes the truncated mutant, SEQ ID NO:1, of the 92 kDa gelatinase having an amino acid sequence as shown in FIG. 2 consisting of residues 106–216 fused to residues 391–443 of the parent molecule.

2. The cDNA which encodes the truncated mutant of the 92 kDa gelatinase of claim 1 containing an additional Met-Gly residue at the N-terminus.

* * * * *